(12) United States Patent
Waldenmaier et al.

(10) Patent No.: US 10,399,086 B2
(45) Date of Patent: Sep. 3, 2019

(54) SYSTEM AND METHOD FOR DISINFECTING MEDICAL WASTE

(71) Applicant: Viradys Medical Waste Solutions, LLC, Greer, SC (US)

(72) Inventors: Eugene W. Waldenmaier, Greenville, SC (US); H. Eugene W. Waldenmaier, Fredericksburg, VA (US); Michael W. Green, Greer, SC (US)

(73) Assignee: Viradys Medical Waste Solutions, LLC, Greer, SC (US)

( * ) Notice: Subject to any disclaimer, the term of this patent is extended or adjusted under 35 U.S.C. 154(b) by 1185 days.

(21) Appl. No.: 14/617,282

(22) Filed: Feb. 9, 2015

(65) Prior Publication Data
US 2016/0228590 A1 Aug. 11, 2016

(51) Int. Cl.
| | | |
|---|---|---|
| A61L 2/04 | (2006.01) | |
| A61L 2/08 | (2006.01) | |
| A61L 2/18 | (2006.01) | |
| B09B 3/00 | (2006.01) | |
| A61L 11/00 | (2006.01) | |
| B02C 19/18 | (2006.01) | |
| B02C 23/12 | (2006.01) | |

(Continued)

(52) U.S. Cl.
CPC ............. B02C 19/186 (2013.01); A61L 2/04 (2013.01); A61L 2/085 (2013.01); A61L 2/18 (2013.01); A61L 11/00 (2013.01); B02C 23/12 (2013.01); B02C 23/18 (2013.01); B07B 15/00 (2013.01); B09B 3/0075 (2013.01); B09B 3/0083 (2013.01)

(58) Field of Classification Search
CPC ....... B02C 19/186; B02C 23/12; B02C 23/18; A61L 2/04; A61L 2/085; A61L 2/18; A61L 11/00; B07B 15/00
USPC .... 241/15, 606, 23, 65; 198/850–853, 803.5
See application file for complete search history.

(56) References Cited

U.S. PATENT DOCUMENTS

| | | |
|---|---|---|
| 4,052,265 A | 10/1977 | Kemp |
| 4,578,185 A | 3/1986 | Wilson et al. |

(Continued)

FOREIGN PATENT DOCUMENTS

| | | |
|---|---|---|
| AU | 199922585 B2 | 8/1999 |
| EP | 0452231 A1 | 10/1991 |

(Continued)

OTHER PUBLICATIONS

Extended European Search Report, dated Mar. 22, 2016.

Primary Examiner — Shelley M Self
Assistant Examiner — Joseph Finan
(74) Attorney, Agent, or Firm — Dority & Manning, P.A.

(57) ABSTRACT

The present disclosure is directed to a system and method for disinfecting medical waste. The method includes shredding the medical waste via a shredder until the medical waste has a predetermined particle size. Further steps include spreading the medical waste onto a heating conveyor and conveying the shredded medical waste through a heating chamber via a heating conveyor. Thus, within the heating chamber, the shredded medical waste is heated via one or more infrared heating elements and at least one additional heating source, e.g. induction heating, such that the medical waste is heated from a plurality of directions. The resulting treated medical waste is biologically inert and clean and can be disposed of in standard commercial garbage or roll-off bins, which are typically located at medical facilities.

19 Claims, 9 Drawing Sheets

(51) Int. Cl.
 *B02C 23/18* (2006.01)
 *B07B 15/00* (2006.01)

(56) References Cited

U.S. PATENT DOCUMENTS

| | | |
|---|---|---|
| 4,984,748 A | 1/1991 | Kimura |
| 5,173,272 A | 12/1992 | Roland |
| 5,226,065 A | 7/1993 | Held et al. |
| 5,252,290 A | 10/1993 | Uesugi |
| 5,270,000 A | 12/1993 | Goldner et al. |
| 5,348,704 A | 9/1994 | Tanaka |
| 5,364,589 A | 11/1994 | Buehler et al. |
| 5,424,033 A | 6/1995 | Roland |
| 5,516,049 A | 5/1996 | Zoncada |
| 5,523,052 A | 6/1996 | Bridges et al. |
| 5,582,793 A | 12/1996 | Glazer et al. |
| 5,799,883 A | 9/1998 | Lewis et al. |
| 6,726,136 B2 | 4/2004 | Swisher, Jr. et al. |
| 7,001,512 B1 | 2/2006 | Newsome |
| 7,361,303 B2 | 4/2008 | Kantor et al. |
| 8,562,793 B2 | 10/2013 | Novak |
| 2007/0204512 A1* | 9/2007 | Self .............. C10J 3/66 48/197 FM |
| 2009/0004051 A1 | 1/2009 | Firestone et al. |
| 2010/0301147 A1* | 12/2010 | Harkess .......... A61L 11/00 241/23 |
| 2013/0175373 A1 | 7/2013 | Morgan et al. |
| 2013/0199918 A1* | 8/2013 | Jones ............ C10B 57/08 201/6 |
| 2013/0306763 A1 | 11/2013 | Carmel |

FOREIGN PATENT DOCUMENTS

| | | |
|---|---|---|
| EP | 0393231 B1 | 12/1991 |
| EP | 0398850 B1 | 3/1995 |
| EP | 2666812 A1 | 11/2013 |
| JP | H 04327848 A | 11/1992 |
| JP | 2006 314698 | 11/2006 |
| JP | 2011 110550 | 6/2011 |
| WO | WO 03/078897 A1 | 9/2003 |
| WO | WO 2010/001476 A1 | 1/2010 |
| WO | WO 2012/003507 A1 | 1/2012 |

\* cited by examiner

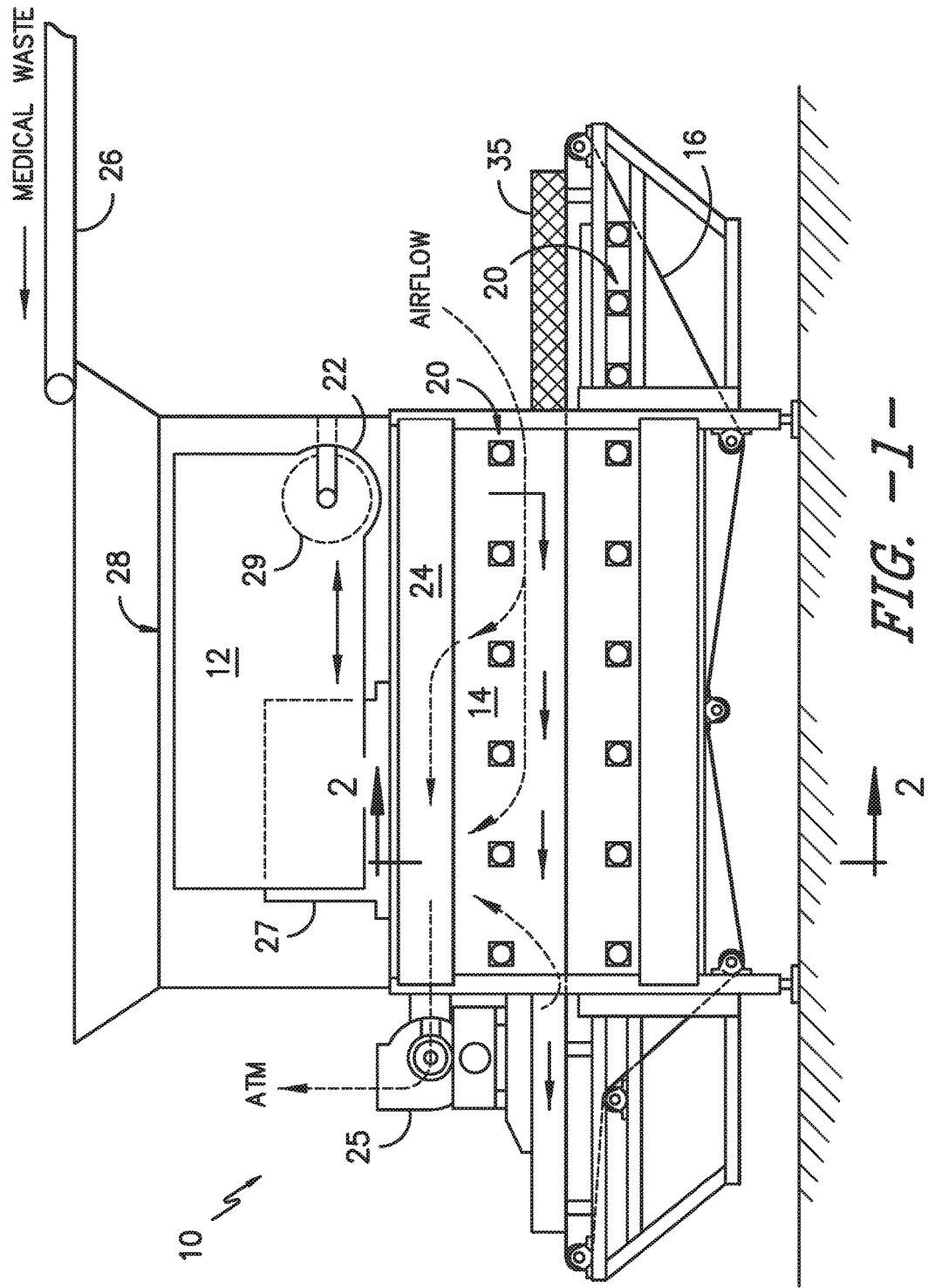

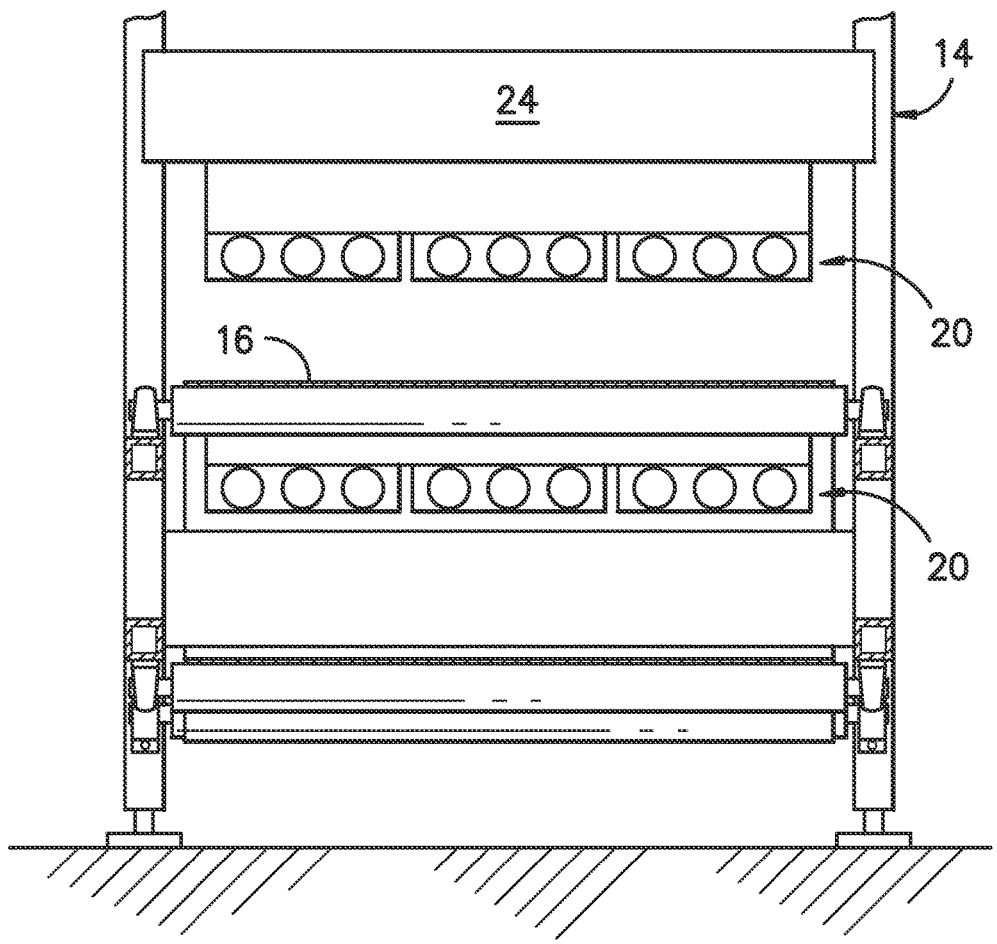
FIG. -2-

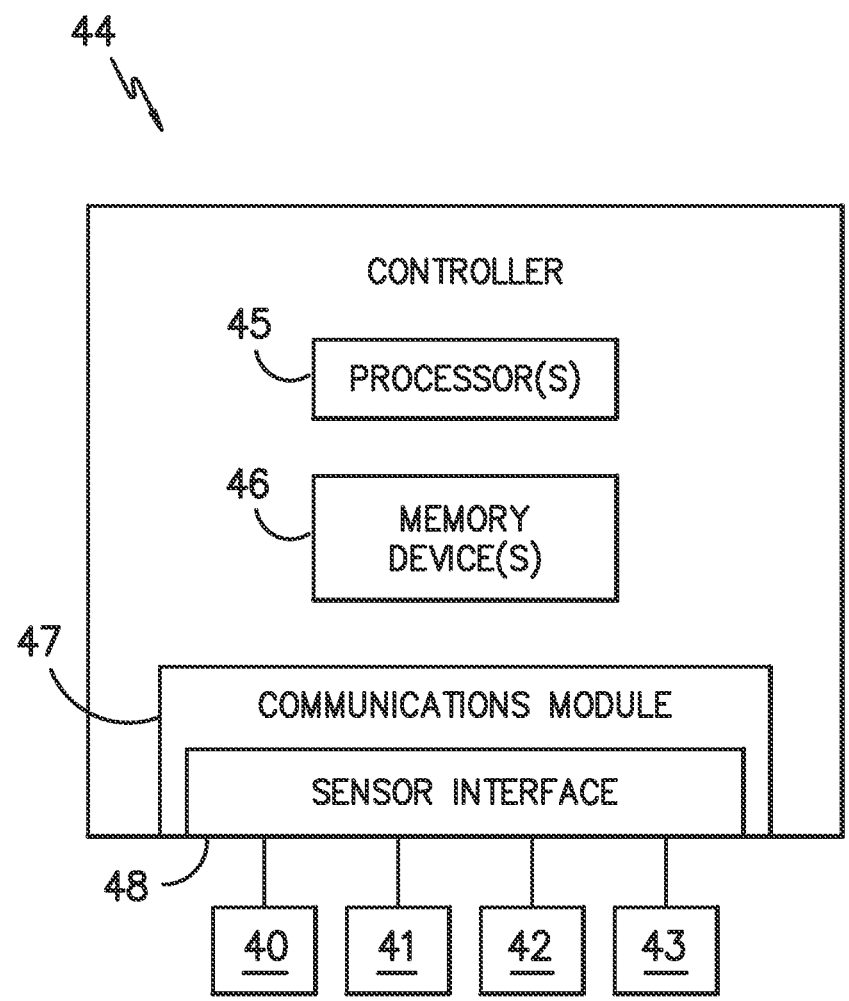
FIG. -3-

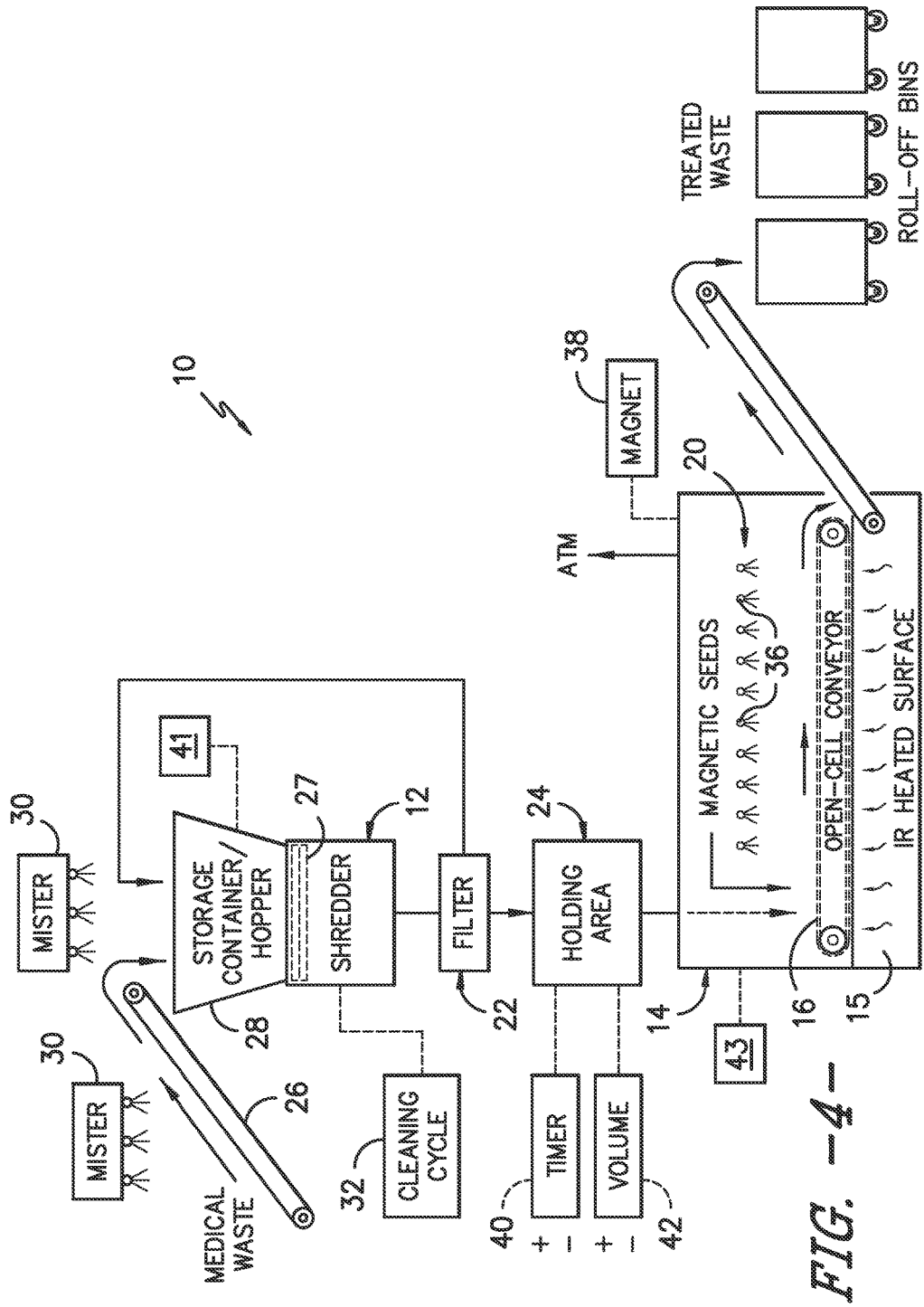
FIG. -4-

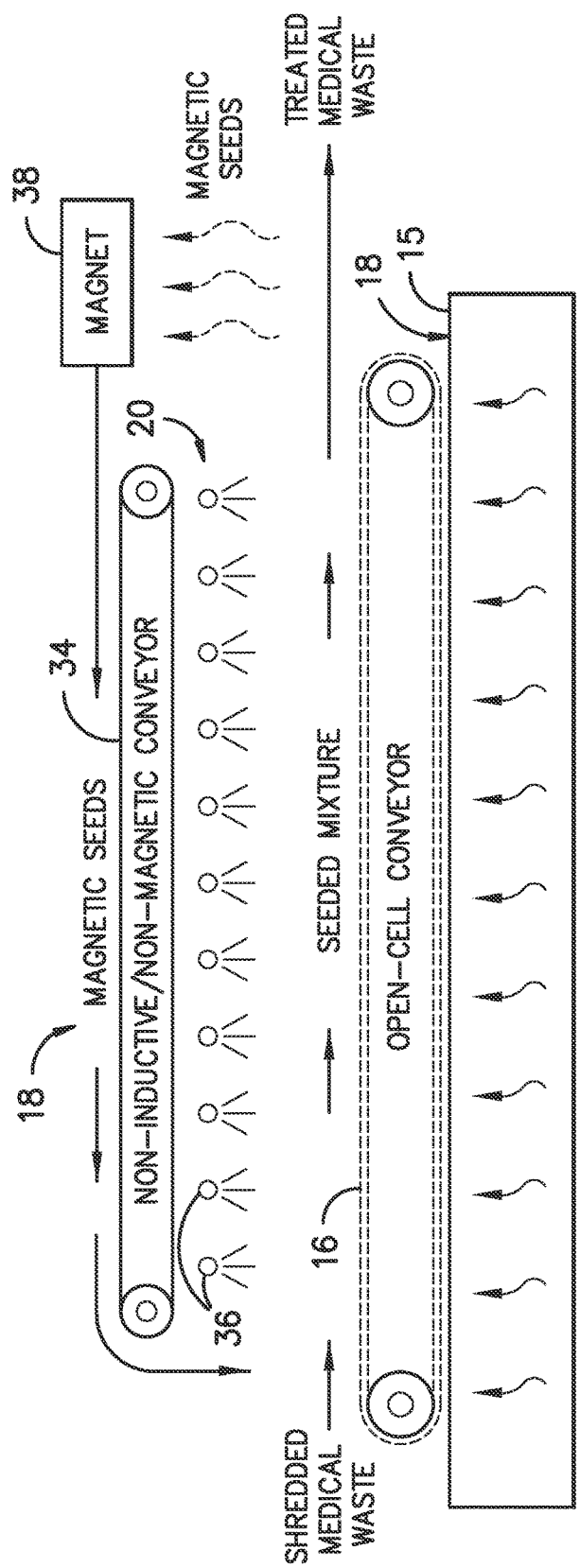
FIG. -5-

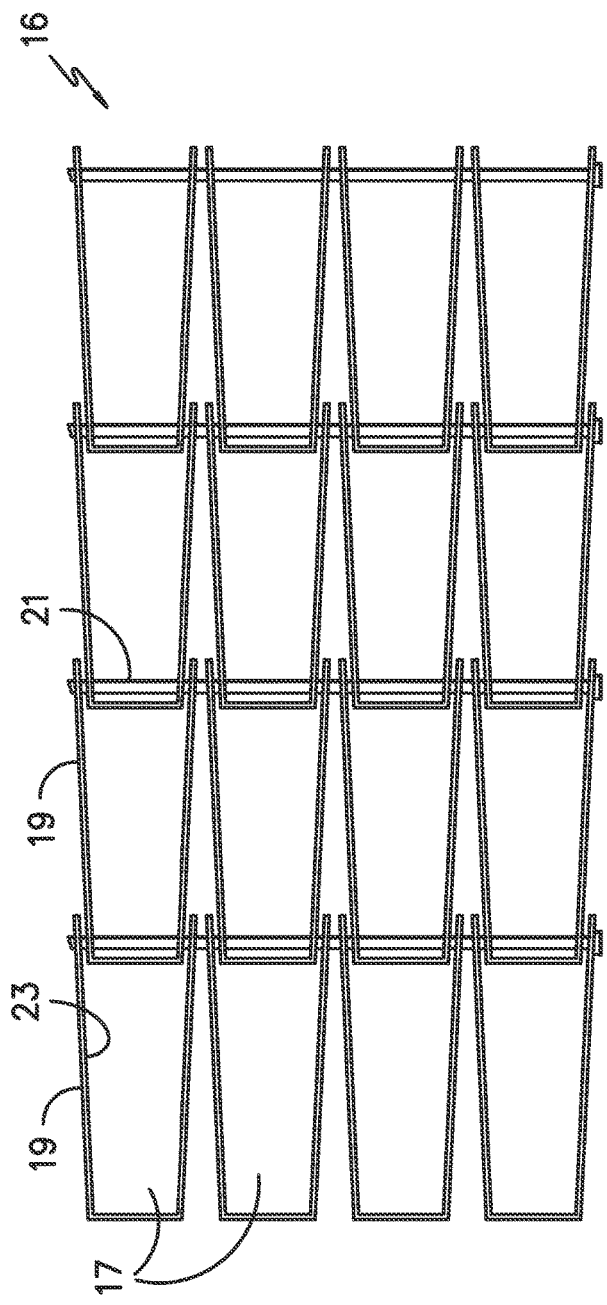
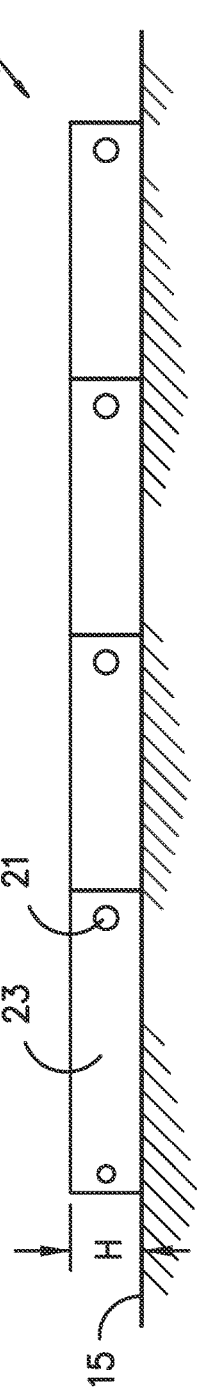
FIG. -6-
FIG. -7-

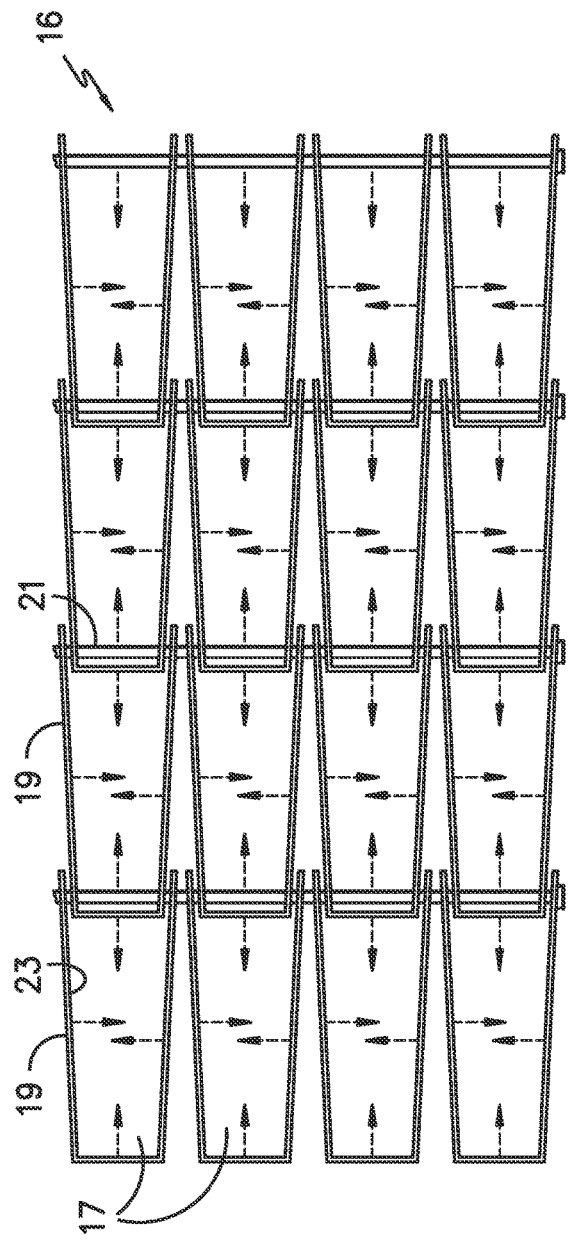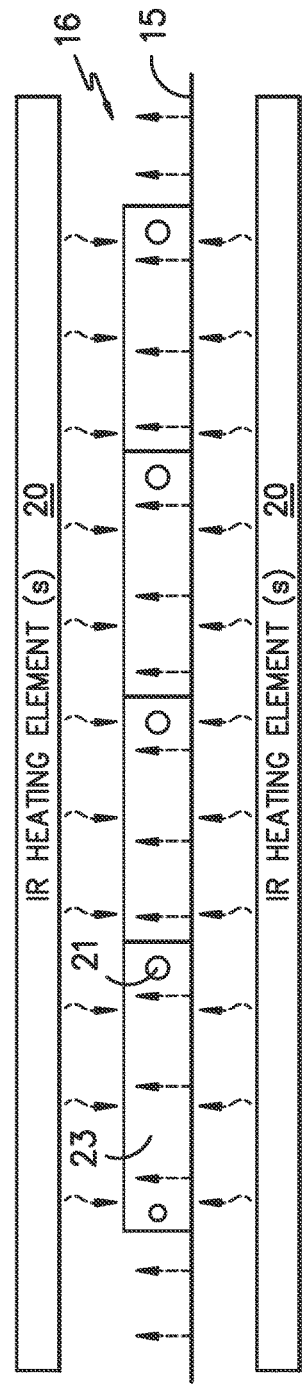

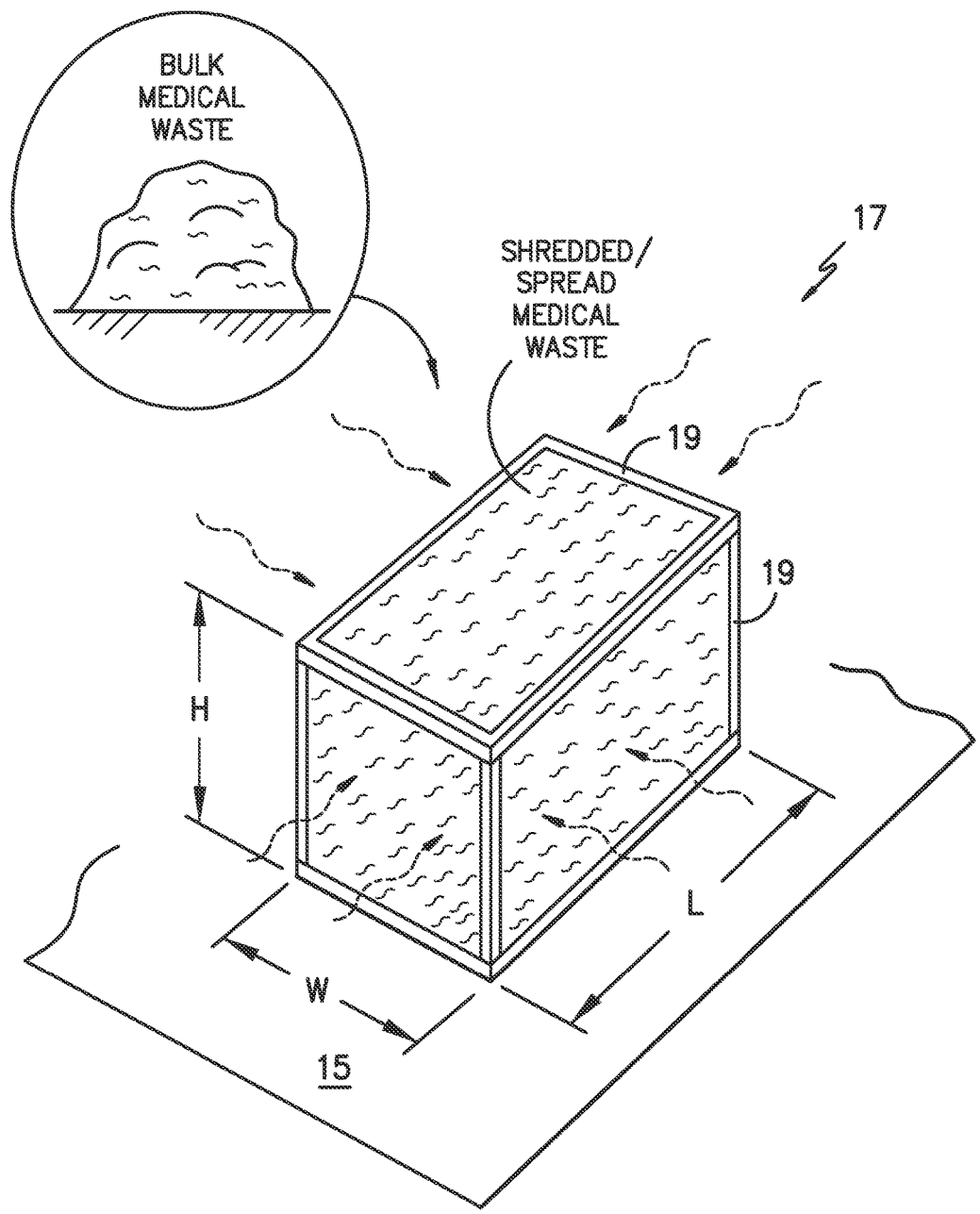
FIG. -10-

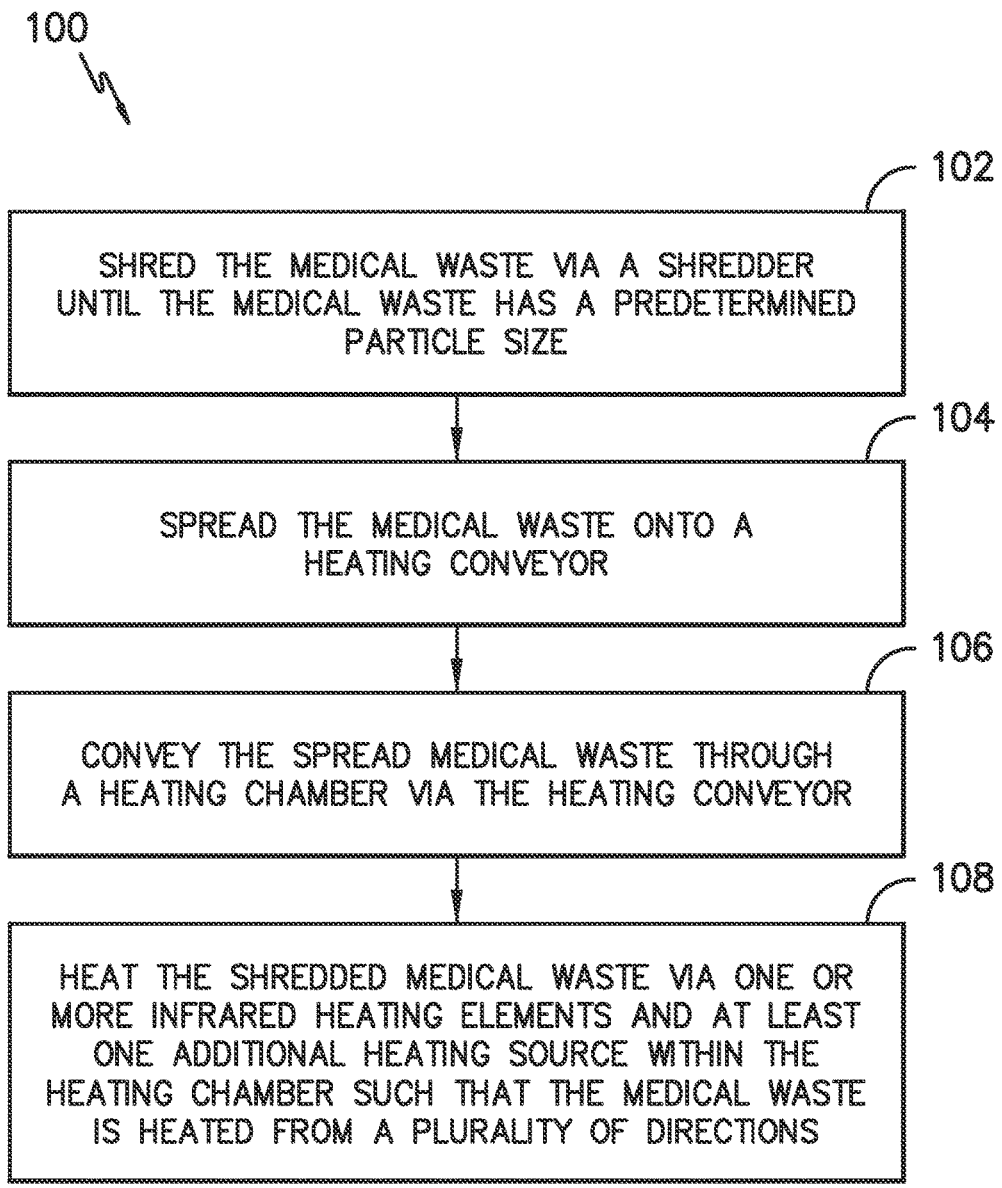
FIG. -11-

SYSTEM AND METHOD FOR DISINFECTING MEDICAL WASTE

FIELD OF THE INVENTION

The present subject matter relates generally to disinfecting medical waste and, more particularly, to systems and methods for disinfecting medical waste on-site at a medical facility using induction and/or infrared heating.

BACKGROUND OF THE INVENTION

Proper disposal of medical waste is required for health care facilities, such as hospitals, medical practices, veterinary offices, and/or other similar facilities. Thus, typical health care facilities employ one or more of the following methods for medical waste disposal: on-site incineration (although use is continually declining due to regulatory and/or environmental pressures), on-site steam auto-claving and later shipment to a landfill, off-site treatment including, but not limited to chemical treatment, steam auto-claving and microwave treatment, and/or combinations thereof.

Problems associated with conventional medical waste disposal, much like the disposal of solid wastes in general, are becoming increasingly acute. For example, although on-site incineration and/or on-site steam auto-claving can decontaminate medical waste effectively, the processes can be complex, time-consuming, and expensive. In addition, many conventional disinfecting systems are not automated and may cause potential hazardous conditions to personnel handling the medical waste. Further, many health care facilities have been forced to turn to off-site companies to supply storage bins for future pickup and eventual disinfection prior to disposal at a landfill. Such off-site disposal can lead to problems, such as potential spills, accidents, and/or an increase in liability exposure during handling and shipment.

The October 2014 Ebola breakout/scare in Dallas, Tex., where days' worth of Ebola-contaminated medical waste was stored in a separate isolation room without any means of elimination, is one example that illuminates medical waste disposal concerns. Current off-site disinfection services have not put into place contingencies for such potential pandemics. Further, off-site disinfection may introduce dangerous contaminants from isolation into a greater population and may also bring such contaminants into settings (e.g. health clinics) that are neither prepared nor equipped to combat such health issues.

Accordingly, there is a need for an improved system and method that addresses the aforementioned issues. More specifically, a system and method for disinfecting medical waste on-site at a medical facility that utilizes infrared heating and at least one additional heating source would be advantageous.

BRIEF DESCRIPTION OF THE INVENTION

Aspects and advantages of the invention will be set forth in part in the following description, or may be obvious from the description, or may be learned through practice of the invention.

In one aspect of the present disclosure, a method for disinfecting medical waste on-site at a medical facility is provided. The method includes shredding the medical waste via a shredder until the medical waste has a predetermined particle size. Further steps include spreading the medical waste onto a heating conveyor and conveying the shredded medical waste through a heating chamber via a heating conveyor. The shredded medical waste is heated via one or more infrared heating elements and at least one additional heating source within the heating chamber such that the medical waste is heated from a plurality of directions. Thus, the resulting treated medical waste is biologically inert, clean and can be disposed of in standard commercial garbage or roll-off bins, which are typically located at medical facilities.

In one embodiment, the heating conveyor is an open-cell conveyor that is configured to provide heat to the medical waste via a plurality of methods. For example, the open-cell conveyor separates the waste and allows the heat of the infrared heating sources to more efficiently reach the center of the waste. In addition, as the open-cell conveyor heats up, heat from the conveyor also heats the waste.

In additional embodiments, the step of heating the shredded medical waste via the at least one additional heating source within the heating chamber further includes heating the shredded medical waste via at least one induction heating source. In certain embodiments, for example, the additional induction heating source may come from the placing the open-cell conveyor in thermal contact with a bottom surface of the heating chamber, wherein the bottom surface comprises a ferric material. In another embodiment, the additional induction heating source may include seeding the shredded medical waste with a one or more magnetic materials and heating the seeded medical waste via an inductive field. In such an embodiment, the method may also include removing the one or more magnetic materials after heating via one or more magnets.

In still further embodiments, the method further includes filtering the shredded medical waste via a filter or a screen, wherein shredded medical waste having a particle size equal to or less than the predetermined particle size is transported to the heating conveyor, and wherein shredded medical waste having a particle size greater than the predetermined particle size is recycled back to the shredder for subsequent re-shredding.

In another embodiment, before shredding, the method may also include transporting the medical waste to a storage container or hopper via a storage conveyor. Thus, the storage container can accumulate a certain amount of medical waste before allowing the medical waste to pass through the shredder.

In further embodiments, the method may include various safety features imposed throughout the disinfecting process. For example, in a particular embodiment, the method may include spraying the medical waste with a disinfecting spray via a mister prior to or during shredding. The disinfecting spray is configured to mitigate any potential hazards posed to maintenance and/or repair personnel that may be handling the waste. The spray may also reduce dust that is generated through the disinfection process. In addition, the method may also include cleaning the shredder by running a plurality of disinfectant, absorbing materials therethrough, e.g. in between shredding cycles. Such cleaning cycles also further ensure the safety of maintenance and/or repair personnel.

In another embodiment, after shredding the medical waste, the method may further include holding the medical waste in a holding area for a predetermined time period or until a certain volume of waste is accumulated. For example, in one embodiment, the holding area may contain one or more sensors configured to measure an amount of waste contained therein. As such, the holding area is configured to hold the waste until a certain volume has accumulated so as to prevent overflow and increase efficiency.

In additional embodiments, the method may also include varying a temperature of the heating chamber based upon one or more characteristics of the shredded medical waste being conveyed therethrough. The characteristics of the waste may include, for example, volume, density, type, composition, particle size, moisture, and/or any other similar characteristic.

In another aspect, the present disclosure is directed to a method for disinfecting medical waste on-site at a medical facility. More specifically, the method includes shredding the medical waste to a predetermined particle size. Another step includes spreading the medical waste within a heating chamber. Within the heating chamber, the shredded medical waste may be heated via one or more infrared heating elements and at least one additional heating source within the heating chamber such that the medical waste is heated from a plurality of directions.

In still another aspect, the present disclosure is directed to a system for disinfecting medical waste on-site at a medical facility. The system includes a shredder, a spreader or leveler, and a heating chamber. The shredder is configured to shred the medical waste until the medical waste has a predetermined particle size. The spreader is configured to spread the shredded medical waste onto an open-cell conveyor. In addition, the heating chamber is configured to disinfect the shredded medical waste. More specifically, the heating chamber includes one or more infrared heating elements and at least one additional heating source. Thus, the open-cell conveyor transports the shredded medical waste through the heating chamber while the one or more infrared heating elements and the additional heat source provide heat to the shredded medical waste so as to provide a suitable amount of disinfecting heat to the shredded medical waste within the heating chamber.

In one embodiment, the system may also include a filter operatively coupled to the shredder. Thus, the filter is configured to recycle medical waste having a particle size greater than the predetermined particle size for subsequent re-shredding.

In another embodiment, the system may also include an additional conveyor configured to transport the medical waste to a storage container before shredding. In addition, the system may include a mister configured to spray the medical waste with a disinfecting spray prior to shredding.

In a further embodiment, the system may also include a holding area configured to hold or store the shredded medical waste after shredding for a predetermined time period or until a certain volume of waste is accumulated. As such, the holding area is configured to control the shredder when the waste volume is too high, e.g. by turning off the shredder function, or when the waste volume is too low, e.g. by turning on the shredder function.

In additional embodiments, the one or more infrared heating elements may include infrared heating lamps configured above the open-cell conveyor. Further, the one or more inductions sources may include an induction heating conveyor configured above the infrared heating lamps and one or more magnetic materials being transported thereon. Thus, the induction heating conveyor, being in an inductive field, is configured to inductively heat and transport the magnetic materials to the open-cell conveyor containing the shredded medical waste. As such, the heated magnetic materials provide induction heating to the shredded medical waste. The method may also include removing the magnetic materials from the shredded medical waste via a magnet after disinfection of the waste is complete.

In still another embodiment, the one or more induction sources may include a bottom surface of the heating chamber, wherein the bottom surface comprises a ferric or iron-containing material.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of a system for disinfecting medical waste according to the present disclosure;

FIG. 2 illustrates a cross-sectional view of the system of FIG. 1 along line 2-2;

FIG. 3 illustrates block diagram of one embodiment of a controller configured to operate the system according to the present disclosure;

FIG. 4 illustrates a process flow diagram of one embodiment of a system for disinfecting medical waste according to the present disclosure;

FIG. 5 illustrates a detailed view of the heating chamber of FIG. 3;

FIG. 6 illustrates a top view of one embodiment of an open-cell conveyor used in the system for disinfecting medical waste according to the present disclosure;

FIG. 7 illustrates a side view of the open-cell conveyor of FIG. 6;

FIG. 8 illustrates a top view of another embodiment of an open-cell conveyor used in the system for disinfecting medical waste, particularly illustrating a plurality of heating sources heating the medical waste from multiple directions according to the present disclosure;

FIG. 9 illustrates a side view of the open-cell conveyor of FIG. 8;

FIG. 10 illustrates a perspective view of one embodiment of an individual cell of the open-cell conveyor according to the present disclosure; and FIG. 11 illustrates a flow diagram of one embodiment of a method for disinfecting medical waste according to the present disclosure.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure is directed to a system and method for disinfecting medical waste. More specifically, the system includes a two-stage, shred-to-disinfection device having a shredder, a spreader, an open-cell conveyor, and a heating chamber. The shredder is configured to shred the medical waste to a predetermined particle size. For example, in certain embodiments, the shredder shreds the waste to a particle size ranging from about 0.25 inches to about 2 inches, more particularly about 0.5 inches. The waste particles are then divided and spread to a plurality of cells of the open-cell conveyor that transports the shredded medical waste through the heating chamber. Within the heating chamber, the shredded medical waste is heated via a combination of heating sources, e.g. infrared and induction heating sources. More specifically, in one embodiment, a plurality of infrared heating lamps and the bottom surface of the heating chamber may provide the desired combination of heating to disinfect the waste. Still additional embodiments are described and discussed in detail herein. The resulting treated medical waste is inert and can be disposed of in standard commercial garbage or roll-off bins.

The present disclosure provides many advantages not present in the prior art. For example, the system and method described herein provides a cost-effective solution to waste disposal that permits on-site disposal of medical waste and ensures disinfection at the facility. More specifically, shredding and spreading of the medical waste produces a non-identifiable by-product that reduces the waste area by up to 80% and allows use of regular commercial waste trucks for the transportation of the treated waste. The shredding and spreading of the waste also allows the infrared heating sources to effectively penetrate the entire waste depth so as to effectively eliminate the hazards associated with the waste. In addition, the open cell conveyor provides transport of the waste through the heating chamber as well as effective and efficient heating from all directions, thereby minimizing the time of penetration (and thus disinfection) throughout the waste. Further, the system of the present disclosure is compact, e.g. occupying an area of less than about fifteen feet (15 ft) by about six feet (6 ft) with a height that can be designed to meet the customer needs. In addition, the system can be operated using standard commercial (e.g. 220V or 440V power) with no need for special or additional electrical requirements.

Referring now to the drawings, FIGS. 1-4 illustrate various components of a system 10 for disinfecting medical waste according to the present disclosure. As used herein, medical waste is broadly defined as any solid or liquid waste that is generated in the diagnosis, treatment, or immunization of human beings and/or animals. As shown, the system 10 includes a shredder 12 mounted above a heating chamber 14. In alternative embodiments, the shredder 12 may be mounted adjacent to the heating chamber 14 rather than above the chamber 14 or at any other suitable location. The shredder 12 may also be configured with a storage container 28 or hopper that stores the waste for a certain amount of time, e.g. until a certain volume of waste has accumulated. For example, waste can be transported to the system 10, e.g. via a conveyor 26 or directly by a user, from a storage location and/or a loading zone, at which time, operation of the system 10 can be controlled manually or via a controller 44. For example, once enough waste has accumulated in the storage container 28, e.g. as determined via sensor 41, the controller 44 commences operation by transferring a certain volume of waste to the shredder 12. More specifically, in certain embodiments, the system 10 may include a user interface that unlocks the unit such that a user can initiate operation of the system 10 via the controller 44 after medical waste is provided thereto.

More specifically, as shown in FIG. 3, a block diagram of one embodiment of a controller 44 configured to control operation of the system 10 according to the present disclosure is illustrated. As shown, the controller 44 may include one or more processor(s) 45 and associated memory device(s) 46 configured to perform a variety of computer-implemented functions (e.g., performing the methods, steps, calculations and the like and storing relevant data as disclosed herein). Additionally, the controller 44 may also include a communications module 47 to facilitate communications between the controller 44 and the various components of the system 10. Further, the communications module 47 may include a sensor interface 48 (e.g., one or more analog-to-digital converters) to permit signals transmitted from the various system sensors 40, 41, 42, 43 to be converted into signals that can be understood and processed by the processors 45. Even though four sensors are illustrated in the system of FIG. 3, it should be understood that any number and/or type of sensor is within the spirit and scope of the invention. Further, it should be appreciated that the sensors 40, 41, 42, 43 may be communicatively coupled to the communications module 47 using any suitable means. For example, as shown in FIG. 3, the sensors 40, 41, 42, 43 are coupled to the sensor interface 48 via a wired connection. However, in other embodiments, the sensors 40, 41, 42, 43 may be coupled to the sensor interface 48 via a wireless connection, such as by using any suitable wireless communications protocol known in the art. As such, the processor 45 may be configured to receive one or more signals from the sensors 40, 41, 42, 43.

As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 46 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 46 may generally be configured to store suitable computer-readable instructions that, when implemented by the processor(s) 45, configure the controller 44 to perform various functions including, but not limited to, transmitting suitable control signals to the system 10 and various other suitable computer-implemented functions.

Referring particularly to FIG. 4, the system 10 may also include a mister 30 configured to spray the medical waste with a disinfecting spray at any suitable time during treatment. For example, as shown, the mister 30 sprays the waste prior to shredding, e.g. as the waste is being transported to the storage container 28 via conveyor 26. In further embodiments, the mister 30 may spray the waste within the storage container 28. Thus, the disinfectant spray can be used to mitigate any potential hazards to maintenance and/or repair personnel. It should be understood that the disinfecting spray may be any suitable spray now known or later developed in the art, including sprays that include, at least in part, water, sodium hypochlorite, phenols, ammonium compounds, hydrogen peroxide, botanicals, silver di-hydrogen citrate, or similar, or any combinations thereof. Thus, the mister 30 is configured to minimize dust created during the disinfection process and provide surface disinfection to the waste. In still additional embodiments, the mister 30 may be configured to spray a disinfectant spray upon shutdown and/or prior to maintenance.

In certain embodiments, the shredder 12 may also be configured with a cleaning cycle 32. As such, the controller 44 may implement the cleaning cycle 32 whenever deemed necessary, e.g. between a certain number of shredding cycles, when initiated by a user, etc. More specifically, the cleaning cycle 32 may include spraying a disinfectant spray through the shredder 12, running a plurality of specialized absorbent materials soaked in disinfectant spray through the shredder 12, and/or any other suitable cleaning process. Such cleaning cycles further ensure the safety of maintenance and repair personnel and mitigate cross-contamination between cycles.

After initiation, the shredder 12 shreds the medical waste to a predetermined particle size. For example, in certain embodiments, the shredder 12 output size can be driven by an optional screen or filter 22 that is placed between the shredder 12 and the discharge. More specifically, as waste is brought into the hopper 28 (i.e. typically in bulk), the system may include a rammer 27 which pushes the waste into a rotating cylinder 29 of the shredder 12 having multiple blades, i.e. knives. The blades work with slots in the floor to cut and/or shred the waste. Shredded medical waste having an appropriate particle size can then pass through the screening filter 22, e.g. via gravity, to the heating chamber 14 or in some embodiments, holding area 24. If the waste particle size is too large to pass through the filter 22, the waste is returned or recycled to the shredder 12 and shredded further until the particle size is sufficiently small to fall through the screen opening. It should be understood that the filter size may depend upon the application and/or varying characteristics of the waste, such as for example, volume, density, type, composition, particle size, and/or similar. As such, in certain embodiments, the screen size of the filter 22 may range from about 0.25 inches to about 5 inches, more preferably from about 0.5 inches to about 1 inch.

In additional embodiments, the shredder 12 may also include one or more seals at the input and output locations that are configured to trap pathogens, particulates, odors, and/or other hazards from escaping the shredder 12 during operation. For example, in certain embodiments, the input seal of the shredder 12 may comprise a top or lid and/or a closed conveyor system.

As mentioned, the system 10 may also include a holding area 24 located between the screening filter 22 and the heating chamber 14 as shown in FIGS. 1, 2, and 4. The holding area 24 integrates the shredder 12 with the heating chamber 14 and holds the waste until the heating chamber 14 is preheated and operationally ready to commence the disinfection process. More specifically, the holding area 24 is configured to identify the amount of waste contained therein. For example, in one embodiment, the holding area 24 may contain one or more sensors 40, 42 configured to detect a time period since a previous shredding cycle and/or a volume of waste contained therein. As such, in one embodiment, the holding area 24 is configured to accumulate a certain volume of waste before allowing the shredder 12 to initiate operation.

More specifically, a lower-limit sensor can activate the shredder 12 when the sensor detects a certain low volume of medical waste (e.g. less than 50% full). Similarly, an upper-level sensor can disable the shredder 12 when the sensor senses that the waste has reached a full level so as to prevent waste overflow in the shredder 12. In another embodiment, the holding area 24 is configured to hold the shredded medical waste for a predetermined time period before transporting the waste to the heating chamber 14, e.g. a time sufficient to allow the heating chamber 14 to preheat to a certain temperature. For example, in certain embodiments, the holding area 24 is configured to hold the waste until the heating chamber 14 reaches a temperature sufficient to disinfect the waste, e.g. from about 160° C. (Celsius), as determined by temperature sensor 43. More specifically, the temperature of the heating chamber 14 can be chosen such that it is high enough to kill biologics, but low enough for safe handling, i.e. to maintain a low fire risk and to prevent release of volatile organic compounds (VOCs).

From the holding area 24, the shredded medical waste can then be spread to a predetermined depth within and upon an open-cell conveyor 16 that passes through the heating chamber 14. Thus, the conveyor 16 collects the waste and pulls it into and through the heating chamber 14. For example, in certain embodiments, the conveyor 16 may pass through a series of mechanical devices 35 (e.g. levelers, spreaders, and/or scrapers) to ensure the waste is at an optimal and/or uniform depth for maximum disinfection efficiency. The mechanical devices 35 may be used to agitate the upper surface of the shredded medical waste on and within the links 19 of the conveyor 16. More specifically, in certain embodiments, the mechanical devices 35 may include one or more of the following devices: levelers, rotating or oscillating scrapers, augers, brushes, and/or paddles so as to further ensure the disinfection process. Thus, the system 10 of the present disclosure can efficiently transfer heat to even the remotest pathogen within the waste.

More specifically, as shown particularly in FIGS. 6-10, the conveyor 16 contains a plurality of open cells 17 within the conveyor belt 16 formed by a series of heated links 19 connected via rods 21 that allow the medical waste to fit within the conveyor 16 and be pulled through the heating chamber 14. For example, FIGS. 6 and 8 illustrate top views of one embodiment of an open cell conveyor 16, with FIG. 8 particularly illustrating heat flow from multiple directions. FIGS. 7 and 9 illustrate side views of the open cell conveyor 16 of FIGS. 6 and 8, respectively. In addition, FIG. 10 illustrates one embodiment of an individual open cell 17 of the conveyor 16 to further illustrate heat flow (as indicated by the dotted arrows) to the shredded and spread medical waste from multiple directions.

As shown in FIGS. 6 and 8, the heated links 19 are joined together via a plurality of parallel rods 21 to form the individual cells 17. Any other suitable connecting means may also be used in addition to the rods 21. More specifically, as shown, the links 19 (and therefore the individual cells 17) have a substantially U-shaped cross-section. In additional embodiments, it should be understood by those of ordinary skill in the art that the links 19 may have any other suitable cross-sectional shape so as to allow the system 10 to operate as described herein. More specifically, as shown particularly in FIG. 8, the cell walls 23 formed by the links 19 facilitates heat transfer to the center of the medical waste within each cell 17 such that all surfaces of the medical waste within each of the cells 17 can be heated by radiation, convection, and/or conductive sources from all directions, which is discussed in more detail below. In addition, the surfaces and material of the conveyor 16 are configured to maximize the heat absorption into the links 19 relative to the selected heating modes, e.g. radiation, convection, or conductive heating sources.

Further, the individual cells 17 of the conveyor 16 may have any suitable size and/or shape that assists with heating of the medical waste and allows efficient operation of the system 10. In addition, the size of the conveyor cell 17 may be a function of many system 10 components, e.g. the system drive and/or the efficiency of the cell 17. For example, if the cell 17 is too long, then the ability to be properly driven around the conveyor path may be problematic. Further, long cells may also result in waste build-up at the back end of the cell as waste is conveyed through the system. In addition, the width of the cell 17 should be designed to ensure efficient heat transfer from the cell walls through the waste. Thus, the optimal cell size provides a smoother drive system, a more uniform distribution of waste within each cell, and efficient heat transfer from the cells to the waste.

In additional embodiments, the cell size design also considers the size of the waste particles, e.g. from about 0.5 inches, since it is an object of the present disclosure for the waste to fit within the cell walls of the conveyor 16 so to increase heat transfer efficiency. In other words, if the cells 17 are too small, then the waste will lie on top of the conveyor cells 17 and will not have contact with the bottom surface 15 of the heating chamber 14, which heats both the waste and the conveyor 16 by conduction.

Accordingly, as shown in FIG. 10, the cells 17 may have a length L of from about one inch (1") to about four inches (4"), a width W of from about one inch (1") to about three inches (3"), and a height H of from about 0.5 inches (0.5") to about one inch (1"). In still further embodiments, the cells 17 may have any suitable dimensions so as to maximize heat transfer and therefore disinfection of the waste. In addition, the waste height within each cell 17 may be from about 75% to about 150% of the cell wall height H. In yet another embodiment, the waste height may be less than 75% or greater than 150% of the cell wall height H.

Within the heating chamber 14, a variety of heating methods may be used to disinfect the medical waste from one or more directions. For example, as shown in FIGS. 4, 5, 8, and 9, one or more infrared heating elements 20 and/or induction heating sources 18 may be used to provide appropriate disinfection to the shredded medical waste. As used herein, the term "infrared" is meant to encompass its broadest ordinary meaning of invisible radiant energy, electromagnetic or heat radiation with longer wavelengths than those of visible light. More specifically, as generally shown in the figures, the infrared heating elements 20 may include a plurality of infrared heating lamps 36 configured above or below (or both) the open-cell conveyor 16 along the length of the heating chamber 14. For example, as shown in FIG. 9, from the top of the heating chamber 14, radiant heat from the infrared heating elements 20 are configured to heat the waste directly such that the waste will heat as it absorbs the radiation. In addition, from the bottom of the heating chamber 14, radiant heat from the infrared heating elements 20 (as well as optional induction heating sources 18, or even heating strips) heats the bottom surface 15 of the heating chamber 14. Thus, as the medical waste contacts the bottom surface 15, the surface 15 supplies heat to the waste via conduction. In addition, in certain embodiments, if no waste is present in the chamber 14, excess heat may be supplied to either or both the conveyor cells 17 via conduction or the chamber environment via convection.

In further embodiments, as shown generally in FIGS. 8 and 9, the cells 17 of the conveyor 16 may also be heated. For example, as shown, the cells 17 of the conveyor 16 may be heated by conduction from the bottom surface 15 of the heating chamber 14. More specifically, as the bottom surface 15 is heated, the surface 15 can provide heat energy to the cells 17 via conduction. In addition, the cells 17 may also be heated by radiation. For example, in addition to heating the waste, the infrared heating elements 20 will radiate (and heat) the conveyor cells 17 in view (line of site) of any one of the infrared heating elements 20. As such, the heat that is absorbed by the conveyor cells 17 can then be resupplied to the medical waste that is in contact with the cells 17 via conduction.

In additional embodiments, the configuration of the infrared heating elements 20 is configured to heat the waste as quickly as possible, e.g. without causing any combustion or VOC release. Thus, the length of the heating chamber 14 can be varied based on the throughput of medical waste that is required. Similarly, the number and/or arrangement of infrared heating lamps 36 may be varied based on the throughput of the waste. Further, operation of the infrared lamps 36 may be controlled via the controller 44 based on the desired heating. For example, in certain embodiments, the infrared heating elements 20 can be set to a higher temperature in the beginning of the disinfection process, e.g. to bring the waste to an initial temperature of approximately 150° C., such that radiation from subsequent heating elements can be set to maintain the initial temperature.

Referring particularly to FIG. 5, at least one additional heating source may be used in addition to the infrared heating elements 20. For example, as shown, one or more induction heating sources 18 may be used in combination with the infrared heating elements 20 to further disinfect the waste. More specifically, as mentioned, the induction heating source 18 may be the bottom surface 15 of the heating chamber 14 as explained in detail herein. More specifically, in a particular embodiment, the bottom surface 15 of the heating chamber 14 may be constructed of a ferric or iron-containing material. Thus, in certain embodiments, the heating conveyor 16 may be in thermal contact with the bottom surface 15 of the heating chamber 14 such that the conveyor 16 and the shredded medical waste are inductively heated. The bottom surface 15 of the heating chamber 14 may be heated using any suitable heat source, including but not limited to thermal radiation, mid-frequency inductive heating, and/or radiation.

In additional embodiments, as shown in FIGS. 4 and 5, the induction heating source 18 may also include an induction heating conveyor 34 configured above the open-cell conveyor 16, e.g. above the infrared heating lamps 36, and having one or more ferric or magnetic materials being transported thereon. As such, the induction heating conveyor 34, being in an inductive field, inductively heats the one or more magnetic materials and transports the magnetic materials to the shredded medical waste on the open-cell conveyor 16 to provide induction heating thereto. Such magnetic materials, being heated via mid-frequency induction fields, are configured to transmit heat to the shredded medical waste to minimize the kill time for viruses and/or bacteria contained within the waste. Once the medical waste has been conveyed through the heating chamber 14 via the open-cell conveyor 16, the magnetic materials can be removed from the medical waste, e.g. via a magnet 38 or any other suitable electromagnetic system.

In many instances, the use of infrared radiation from above provides suitable disinfection of the medical waste in less than about 20 minutes to a rate of 6 Log 10. When heat is applied in both directions (i.e. from the top and bottom of the heating chamber 14), suitable disinfection of the medical waste is achieved in less than about 12 minutes, e.g. about 10 minutes, also to a rate of 6 Log 10.

In further embodiments, the temperature within the heating chamber 14 can be monitored continuously, e.g. via temperature sensor 43. Thus, in certain embodiments, the temperature within the heating chamber 14 can be varied based upon one or more characteristics of the shredded medical waste being conveyed therethrough. The characteristics of the waste may include, for example, volume, density, type, composition, particle size, and/or similar. More specifically, in particular embodiments, since the intensity of the radiation and heat are dynamic and dependent on a number of sensor inputs (e.g. thermocouple heat, infrared heat, optical detector, and/or ionization density), heat can be increased when liquids are sensed indirectly via temperature fluctuations and reduced by heat sensors and ionization as necessary. In addition, the total amount of energy applied can be maintained to ensure suitable disinfection is obtained. Suitable disinfection can vary based on the type and/or amount of medical waste to be treated, but is typically determined based upon one or more of the following factors: temperature, waste density, and/or disinfection time. In addition, the system 10 may include a testing phase to ensure the waste has been treated to known standards. Thus, once suitable disinfection is achieved, the treated medical waste, now shred and inert, can be conveyed to standard commercial garbage or roll-off bins which are typically located at health care facilities and/or other commercial institutions as shown in FIG. 4.

In addition, and referring back to FIG. 1, the system 10 may include a blower 25 or fan configured to circulate air within the heating chamber 14 to further transfer heat throughout the chamber 14. Accordingly, as the conveyor 16 transports the medical waste through the heating chamber 14, upward fluid air pressure (as indicated by the dotted arrows) can be used to dislodge, mix, and/or expose heat in the chamber 14 to all of the particles of the shredded medical waste within the cell walls of the conveyor links 19.

It should also be understood that the system and method of the present disclosure, which combines radiative and conductive heat transfer, provides a time constant to the most remote pathogen of the waste that is substantially less than that of prior art systems, e.g. of from about one minute. As such, the present disclosure provides the desired extinction of live pathogens within a predetermined timeframe, e.g. of from about 10 to about 20 minutes, with a significant safety margin from overheating the waste, which, as mentioned, can result in fires and/or VOC release.

In addition, the amount of power required to disinfect medical waste is dependent upon a number of factors, e.g. waste composition, water content, waste density, infrared adsorption rate, thermal time constant between exposed waste surface and one or more pathogens, etc. Therefore, taking into account such factors, the inventors of the present disclosure have discovered that a power density of about ten kilowatts per meter (10 kW/m$^2$) is required to raise the temperature of the medical waste to required disinfection levels within an acceptable time frame, with a waste depth as described herein.

Referring now to FIG. 11, a flow diagram of a method 100 for disinfecting medical waste is illustrated. As shown at 102, the method 100 includes shredding the medical waste via a shredder until the medical waste has a predetermined particle size. At 104, the method 100 includes spreading the medical waste onto a heating conveyor. At 106, the method includes conveying the spread medical waste through a heating chamber via the heating conveyor. At 108, the method 100 includes heating the shredded medical waste via one or more infrared heating elements and at least one additional heating source within the heating chamber such that the medical waste is heated from a plurality of directions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for disinfecting medical waste on-site at a medical facility, the method comprising:
   providing a medical disinfecting system having a shredder, a heating conveyor, a heating chamber, one or more infrared heating elements and at least one additional heating source;
   shredding the medical waste via the shredder until the medical waste has a predetermined particle size;
   spreading the medical waste onto the heating conveyor, the heating conveyor comprising an open-cell conveyor having plurality of open cells configured to receive the medical waste, each of the open cells defining an exposed top opening and an exposed bottom opening;
   conveying the spread medical waste through the heating chamber via the heating conveyor; and,
   heating the shredded medical waste via the one or more infrared heating elements and the at least one additional heating source within the heating chamber such that the medical waste is heated from a plurality of directions.

2. The method of claim 1, wherein the open-cell conveyor defines a closed perimeter comprising a plurality of heated side walls, the heated side walls configured to provide additional heat to the medical waste.

3. The method of claim 1, wherein heating the shredded medical waste via the at least one additional heating source within the heating chamber further comprises heating the shredded medical waste via at least one induction heating source.

4. The method of claim 3, wherein heating the shredded medical waste via at least one induction heating source further comprises placing the open-cell conveyor in thermal contact with a bottom surface of the heating chamber, wherein the bottom surface comprises a ferric material.

5. The method of claim 3, wherein heating the shredded medical waste via at least one induction heating source further comprises:
   heating one or more magnetic materials via an inductive field; and,
   transporting the one or more magnetic materials to the shredded medical waste; and
   heating the shredded medical waste via the one or more magnetic materials.

6. The method of claim 5, further comprising removing, via one or more magnets, the one or more magnetic materials after heating the shredded medical waste.

7. The method of claim 1, further comprising filtering the shredded medical waste via a filter, wherein shredded medical waste having a particle size equal to or less than the predetermined particle size is transported to the heating conveyor, and wherein shredded medical waste having a particle size greater than the predetermined particle size is recycled back to the shredder.

8. The method of claim 1, further comprising, before shredding the medical waste, transporting the medical waste to a storage container via a storage conveyor.

9. The method of claim 1, further comprising spraying the medical waste with a disinfecting spray via a mister prior to shredding.

10. The method of claim 1, further comprising cleaning the shredder by running a plurality of disinfectant, absorbing materials therethrough.

11. The method of claim 1, further comprising, after shredding but before heating the medical waste, holding the medical waste in a holding area for a predetermined time period or until a certain volume of waste is accumulated.

12. The method of claim 1, further comprising varying a temperature of the heating chamber based upon one or more characteristics of the shredded medical waste being conveyed therethrough, wherein the characteristics of the shredded medical waste comprise one or more of volume, density, type, composition, moisture, or particle size.

13. A system for disinfecting medical waste on-site at a medical facility, the system comprising:
a shredder configured to shred the medical waste until the medical waste has a predetermined particle size;
an open-cell conveyor comprising a plurality of open cells configured to receive the medical waste, each of the open cells defining an exposed top opening and an exposed bottom opening;
a spreader for spreading the shredded medical waste into the open cells of the open-cell conveyor;
a heating chamber configured to disinfect the shredded medical waste, the heating chamber comprising one or more infrared heating elements and at least one additional heating source,
wherein the open-cell conveyor transports the shredded medical waste through the heating chamber while the one or more infrared heating elements and the additional heating source provide heat to the shredded medical waste.

14. The system of claim 13, wherein the at least one additional heating source further comprises at least one induction heating source.

15. The system of claim 14, wherein the at least one induction heating source further comprises a bottom surface of the heating chamber, wherein the exposed bottom opening of the open-cell conveyor is in thermal contact with the bottom surface of the heating chamber.

16. The system of claim 13, wherein the one or more infrared heating elements comprise a plurality of infrared heating lamps configured above or below the open-cell conveyor.

17. The system of claim 14, wherein the at least one induction heating source further comprises an induction heating conveyor configured above the open-cell conveyor and one or more magnetic materials being transported thereon, wherein the induction heating conveyor is in an inductive field that inductively heats the one or more magnetic materials, the induction heating conveyor transporting the one or more magnetic materials to the open-cell conveyor containing the shredded medical waste to provide induction heating to the shredded medical waste.

18. The system of claim 13, further comprising a filter operatively coupled to the shredder, wherein shredded medical waste having a particle size equal to or less than the predetermined particle size is transported to the open-cell conveyor, and wherein shredded medical waste having a particle size greater than the predetermined particle size is recycled back to the shredder.

19. The system of claim 13, further comprising a mister configured to spray the medical waste with a disinfecting spray prior to shredding.

* * * * *